(12) United States Patent
Fang et al.

(10) Patent No.: US 9,622,663 B2
(45) Date of Patent: Apr. 18, 2017

(54) ROTATION TYPE OPTICAL TOMOGRAPHY SCANNER

(71) Applicant: National Chiao Tung University, Hsinchu (TW)

(72) Inventors: Wai-Chi Fang, Hsinchu (TW); Tien-Ho Chen, Hsinchu (TW); Shih Kang, Hsinchu (TW); Shih-Yang Wu, Hisnchu (TW); Ching-Ju Cheng, Hsinchu (TW)

(73) Assignee: National Chiao Tung University, Hsinchu, Taiwan (TW)

( * ) Notice: Subject to any disclaimer, the term of this patent is extended or adjusted under 35 U.S.C. 154(b) by 489 days.

(21) Appl. No.: 14/140,197

(22) Filed: Dec. 24, 2013

(65) Prior Publication Data

US 2014/0187926 A1    Jul. 3, 2014

(30) Foreign Application Priority Data

Dec. 28, 2012   (TW) .............................. 101150914 A

(51) Int. Cl.
*A61B 5/05*    (2006.01)
*A61B 5/00*    (2006.01)

(52) U.S. Cl.
CPC .......... *A61B 5/0064* (2013.01); *A61B 5/0066* (2013.01); *A61B 5/444* (2013.01)

(58) Field of Classification Search
CPC ...... A61B 5/0064; A61B 5/0066; A61B 5/444
See application file for complete search history.

(56) References Cited

U.S. PATENT DOCUMENTS

| | | | |
|---|---|---|---|
| 2002/0033454 A1* | 3/2002 | Cheng ................ | A61B 5/14546 250/339.12 |
| 2010/0249606 A1* | 9/2010 | Ziegler ................ | A61B 5/0091 600/473 |

* cited by examiner

*Primary Examiner* — Jonathan Cwern
(74) *Attorney, Agent, or Firm* — Mintz Levin Cohn Ferris Glovsky and Popeo, P.C.; Peter F. Corless; Steven M. Jensen

(57) ABSTRACT

A rotation type optical tomography scanner is provided, including an illuminating unit disposed on a surface of an object-to-be-detected for emitting incident light to tissues under the surface of the object-to-be-detected; a detecting unit disposed on the object-to-be-detected and rotating around the illuminating unit to receive diffuse light diffused from the tissues under the surface of the object-to-be-detected and generate tissue sensing information; and a positioning unit for generating position information of the rotation type optical tomography scanner. The rotation type optical tomography scanner transmits the sensing information and the position information to a remodel module to rebuild the tissue images under the surface of the object-to-be-detected, thereby expanding the scanning range of the object-to-be-detected.

2 Claims, 3 Drawing Sheets

Image rebuilding (old)

Image rebuilding (new)

ROTATION TYPE OPTICAL TOMOGRAPHY SCANNER

CROSS-REFERENCES TO RELATED APPLICATIONS

This application claims under 35 U.S.C. §119(a) the benefit of Taiwanese Application No. 101150914, filed Dec. 28, 2012, the entire contents of which is incorporated herein by reference.

BACKGROUND OF THE INVENTION

1. Field of the Invention

The present invention relates to optical tomography techniques, and, more particularly, to a rotation type optical tomography scanner.

2. Description of Related Art

Diffuse optical tomography technique is a very promising imaging technique in the field of biomedical optics, which utilizes near infrared to measure the difference of scattering and absorbing level between normal and abnormal tissues in an organism to rebuilt images. The major applications are brain function diagnosis and breast cancer detection.

When a light source and a light detector are attached on the skin, the light projects into tissues through the light source, and a diffusion effect is generated inside the tissues. Then, a portion of the light diffuse to the light detector, by which allowing subsequent image rebuilding hardware or software to rebuild images for obtaining relative information inside the tissues.

However, the number of light sources and light detectors and the relative position would influence the detection range and depth, then the tissue scattering coefficient and absorption coefficient will also influence the derivation of an image rebuilding algorithm. In the present light tomography sensing technique field, many embodiments of diffuse optical tomography sensing technique are achieved by a fixed scanner with huge volume and high cost. In other words, the positions of light sources and light detectors only fixedly target on a single area of the object-to-be-detected in one single sensing process. If an increased area is desired, additional light detectors are necessary. Thus, this method increases the volume and cost of the scanner, and also indirectly limits the efficacy of subsequent images rebuilding and causes a heavy economic burden on those to be examined.

Therefore, in order to achieve the substantial demands of sensing adaptable to different areas of the object-to-be-detected, promoting the completeness of images rebuilding and alleviating the economic burden on those to be examined, it is pressing to develop a new sensing technique.

SUMMARY OF THE INVENTION

In view of the above-mentioned problems of the prior art, the objective of the present invention is to provide a rotation type optical tomography scanner, which diffuses the scanning range of the object-to-be-detected.

The present invention provides a rotation type optical tomography scanner, comprising: an illuminating unit disposed on s surface of an object-to-be-detected for emitting incident light to tissues under the surface of the object-to-be-detected; a detecting unit disposed on the object-to-be-detected and rotating around the illuminating unit to receive diffuse light diffused from the tissues under the surface of the object-to-be-detected and generate tissue sensing information.

The present invention further provides another rotation type optical tomography scanner, comprising: an illuminating unit disposed on a surface of an object-to-be-detected for emitting incident light to tissues under the surface of the object-to-be-detected; a carrier having a light transmission aperture and disposed on the object-to-be-detected, the carrier keeping rotating such that the light transmission aperture rotates around the illuminating unit with the illuminating unit as a center; and a detecting unit disposed on the illuminating to receive diffuse light diffused from the tissues under the surface of the object-to-be-detected and generate tissue sensing information through the light transmission aperture.

The sensing information may comprise an angle of the diffuse light.

Moreover, the carrier may be a disk to carry the detecting unit to rotate around the illuminating unit as a circular motion.

In addition, the rotation type optical tomography scanner according the present invention may comprise a positioning unit for generating position information of the rotation type optical tomography scanner. The optical rotation type optical tomography scanner transmits the sensing information and the position information to an image remodel module to rebuild the tissue images under the surface of the object-to-be-detected by using an algorithm based on the sensing information and the position information.

Because the detecting unit of the rotation type optical tomography scanner according to the present invention is movable, or may utilize a movable light transmission aperture to incorporate with a fixed detecting unit, this is equivalent to disposing plural detecting units around the illuminating unit. Thus the optical rotation type optical tomography scanner can move within a plurality of areas of the object-to-be-detected, and expand the scanning range and promote the image resolution.

BRIEF DESCRIPTION OF DRAWINGS

The invention can be more fully understood by reading the following detailed description of the preferred embodiments, with reference made to the accompanying drawings, wherein.

DETAILED DESCRIPTION OF THE INVENTION

The following illustrative embodiments are provided to illustrate the disclosure according to the present invention, these and other advantages and effects can be apparently understood by those in the art after reading the disclosure of this specification. The present invention can also be performed or applied by other different embodiments. The details of the specification may be on the basis of different points and applications, and numerous modifications and variations can be devised without departing from the spirit according to the present invention.

Figure 1:
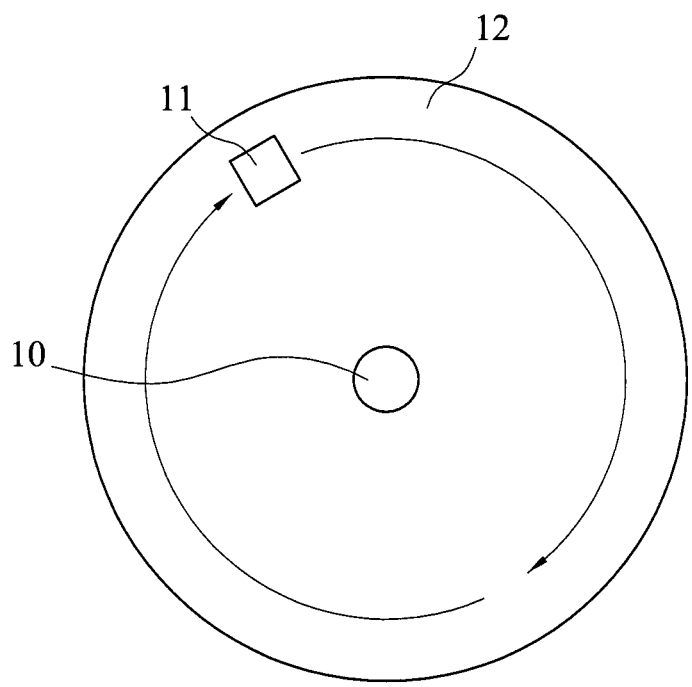
FIG. 1 is a basic structure diagram of a first embodiment of a rotation type optical tomography scanner according to the present invention.
Figure 2:
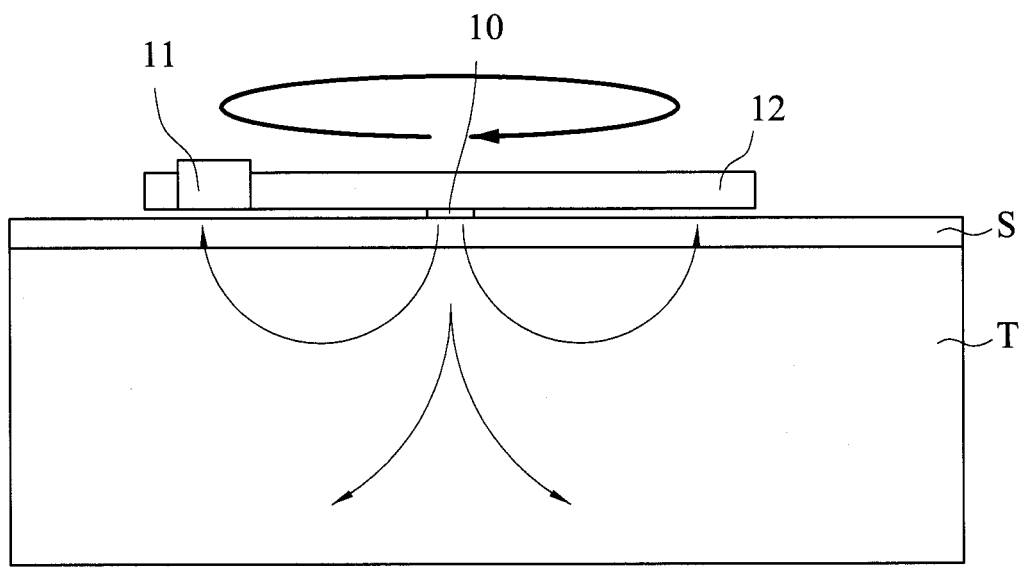
FIG. 2 is a schematic diagram of the first embodiment of the rotation type optical tomography scanner according to the present invention disposed on the object-to-be-detected.

Please refer to FIGS. 1 and 2 to understand a first embodiment of a rotation type optical tomography scanner according to the present invention. FIG. 1 is a basic structure diagram of a first embodiment of a rotation type optical tomography scanner according to the present invention, and FIG. 2 is a schematic diagram of the first embodiment of the rotation type optical tomography scanner according to the present invention disposed on the object-to-be-detected.

The rotation type optical tomography scanner provided according to the present invention is used to scan a surface of an object-to-be-detected, wherein the object-to-be-detected may be a human breast, for example. The optical rotation type optical tomography scanner is disposed on the skin S, which can detect abnormal tissues such as a tumor or cancer cells, if existing, in the tissues T under the skin S.

An illuminating unit 10 is disposed on the surface of the object-to-be-detected, and emits incident light to the tissues T under the skin S. The incident light is scattered or absorbed by the tissues T under the skin S to generate diffuse light.

A detecting unit 11 is disposed on the object-to-be-detected and rotates around the illuminating unit 10 to receive the diffuse light diffused from the incident light onto the tissues T and generate tissue sensing information, wherein the sensing information comprises an angle of the diffuse light.

In an embodiment, the detecting unit 11 takes the illuminating unit 10 as a center to move around within a certain distance. As shown in FIGS. 1 and 2, the rotation type optical tomography scanner according to the present invention may comprise a carrier 12, which can be a disc to carry the detecting unit 11 to perform a circular motion around the illuminating unit 10 with the illuminating unit as a center. In addition, the rotation type optical tomography scanner according to the present invention may also comprise a drive mechanism (not illustrated), which can drive the carrier 12 to rotate such that the detecting unit 11 can perform a circular motion around the illuminating unit 10 with the illuminating unit 10 as a center.

Figure 4:
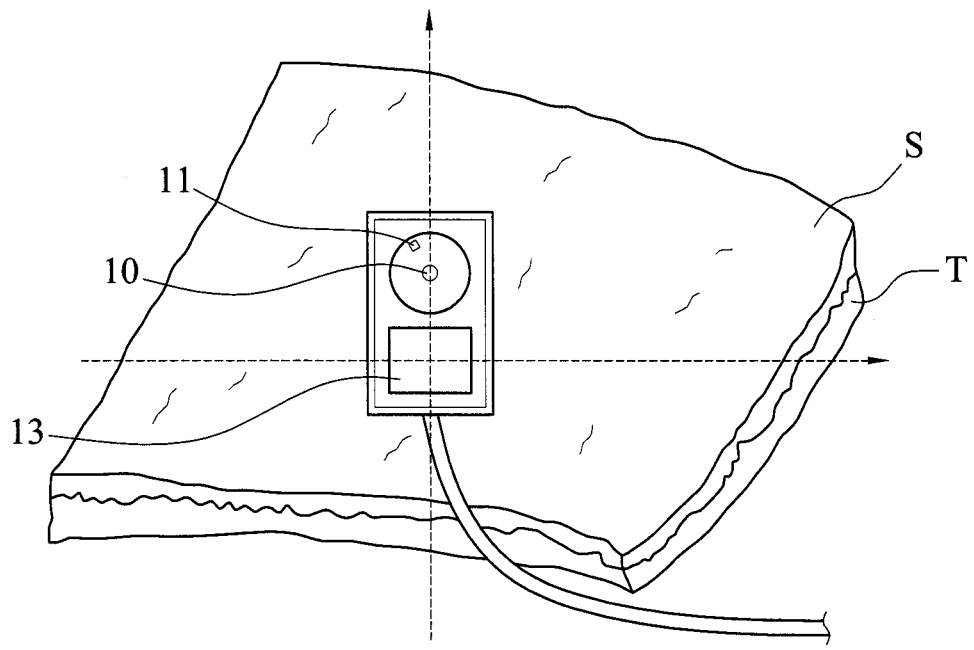
FIG. 4 is a schematic diagram of the rotation type optical tomography scanner according to the present invention in the operation of optical tomography scanning.

Moreover, referring to FIG. 4, the rotation type optical tomography scanner according to the present invention may further comprise a positioning unit 13, which may generate the position information of the rotation type optical tomography scanner. Therefore, the rotation type optical tomography scanner according to the present invention may move on the skin S to detect different areas of tissues T. In addition, the rotation type optical tomography scanner according to the present invention may further transmit the sensing information generated by the detecting unit 11 and the position information generated by the positioning unit to a remodel module (not illustrated), such as a computer or other electronic devices installed with a remodel program which can rebuild images of tissues T based on the sensing information and the position information as shown in FIG. 5.

Figure 5:
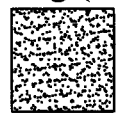
FIG. 5 is a schematic diagram for an image rebuilding performed by the rotation type optical tomography scanner according to the present invention.
Figure 5:
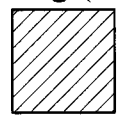
Figure 5:
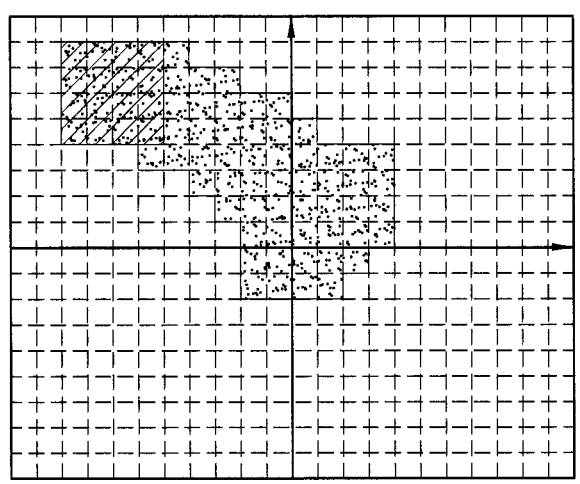

Refer to FIGS. 4 and 5. The rotation type optical tomography scanner is disposed on the surface of the object-to-be-detected, and, in the meanwhile, the positioning unit 13 defines an initial position such as the point crossed by two axes in FIGS. 4 and 5, so when the rotation type optical tomography scanner displaces on the surface of the object-to-be-detected, the positioning unit 13 immediately generates the current position of the rotation type optical tomography scanner. Furthermore, when the rotation type optical tomography scanner repeatedly scans the same area, the new image rebuilding data overwrites the old image rebuilding data. Therefore, except expanding the scanning range, the rotation type optical tomography scanner having a positioning unit can also promote the resolution of the image scan.

Figure 3:
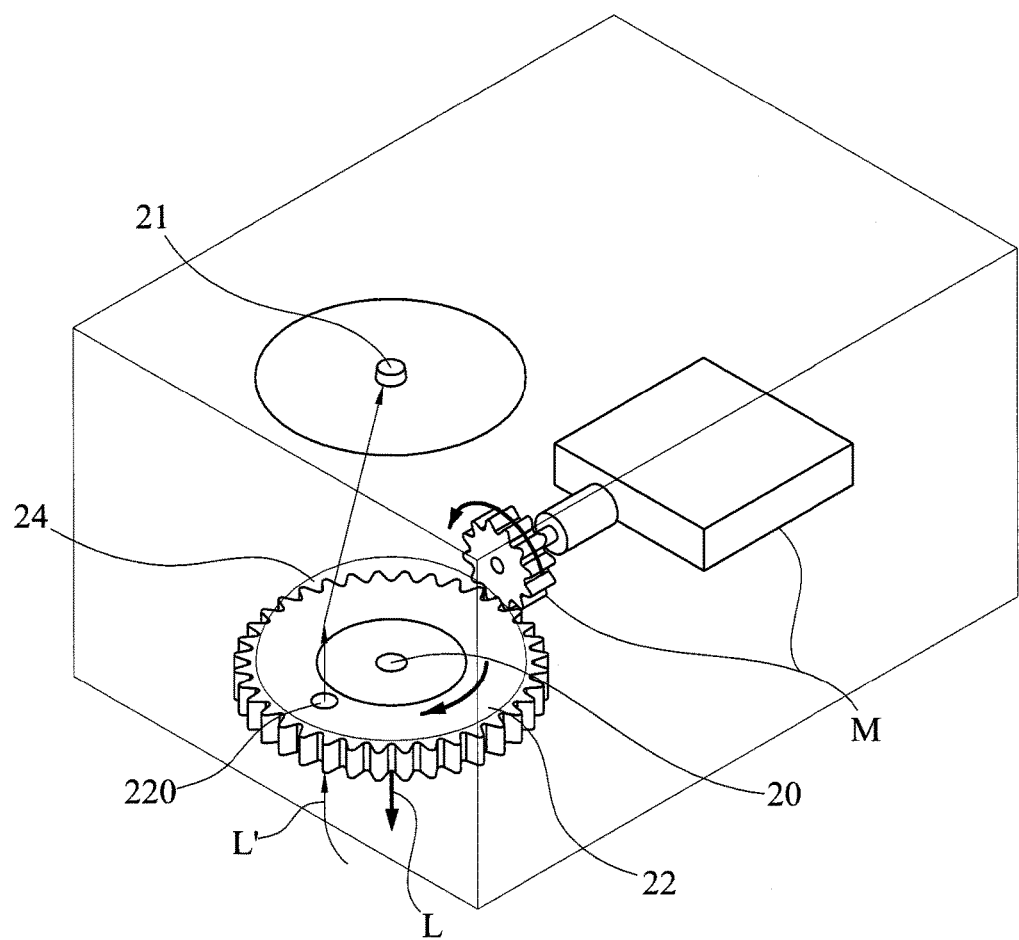
FIG. 3 is a structure diagram of a second embodiment of a rotation type optical tomography scanner according to the present invention.

Further referring to partial technical features as shown in FIGS. 1 and 2 to see FIG. 3 to understand the second embodiment of the rotation type optical tomography scanner in the present invention.

An illuminating unit 20 is disposed on the surface of the object-to-be-detected, and emits incident light L into tissues under the surface of the object-to-be-detected.

A carrier 22 is disposed on the object-to-be-detected and has a light transmission aperture 220. The carrier 22 rotates such that the light transmission aperture 220 moves around the illuminating unit 20. As shown in FIG. 3, the carrier 22 may be a disc with a dentate structure at the edge provided to a drive structure M including a motor, a motion detector and a gear to drive such that the light emission aperture 220 may performs a circular motion around the illuminating unit 20 as a circle by the driving of the drive structure M.

A detecting unit 21 is disposed over the illuminating unit 20, as shown in FIG. 3, and the position corresponds to the illuminating unit 20. The detecting unit 21 receives the diffuse light L' passing a light transmission aperture 220 and diffused from the incident light L onto the tissues under the surface of the object-to-be-detected and generates sensing information.

The rotation type optical tomography scanner according to the present invention may further comprise a convex lens 24 on the carrier 22, which refracts the diffuse light L' passing a light transmission aperture 220 to a detecting unit 21 over the illuminating unit 20.

Therefore, the difference between the first and the second embodiments of the rotation type optical tomography scanner according to the present invention is that in the first embodiment a detecting unit 11 performs a circular motion around an illuminating unit 10 as a center, while in the second embodiment a detecting unit 21 keeps still over the illuminating unit 20, the one rotates is a carrier 22 having a light transmission aperture 220 and is disposed on the object-to-be-detected. The carrier 22 performs a circular motion through the light transmission aperture 220 around an illuminating unit 20 as a center so that the diffuse light L' diffused from the incident light L scattered or absorbed by the tissues under the skin proceeds to the detecting unit 20.

In addition, in the second embodiment, the rotation type optical tomography scanner may also comprise a positioning unit, (not illustrated in the drawings, may be referred to the positioning unit 13 shown in FIG. 4) which generates the position information of the rotate type optical rotation type optical tomography scanner. Thus, when the rotation type optical tomography scanner moves on the surface of the object-to-be-detected, which area the present detecting unit detects is of the object-to-be-detected can be known. Similarly, in the second embodiment, the rotation type optical tomography scanner according to the present invention may further transmit the sensing information generated by the detecting unit 11 and the position information generated by the positioning unit to a remodel module (not illustrated), such as a computer or other electronic devices installed with a remodel program which can rebuild images of tissues T based on the sensing information and the position information as shown in FIG. 5.

In summary, since the rotation type optical tomography scanner according to the present invention has a detecting unit rotates around the illuminating unit as a center (or a light transmission aperture rotates around the illuminating unit), this is equivalent to an optical rotation type optical tomography scanner having a plurality of detectors disposed around the illuminating unit. Furthermore, the rotation type optical tomography scanner according to the present invention has a positioning unit so that it is able to move on the object-to-be-detected to detect the tissues of different areas under the surface of the object-to-be-detected. Therefore, the rotation type optical tomography scanner according to the present invention has advantages of simple structure, and also eliminates the drawback that the sensing technique in the prior art is not able to sense a plurality of different areas of the object-to-be-detected continuously and fast, and further break through the drawback that the completeness of images rebuilding in the prior art is insufficient by the performed integrated images rebuilding.

The foregoing descriptions of the detailed embodiments are only illustrated to disclose the features and functions according to the present invention and not restrictive of the scope according to the present invention. It should be understood to those in the art that all modifications and variations according to the spirit and principle in the disclosure according to the present invention should fall within the scope of the appended claims.

What is claimed is:

1. A rotation type optical scanner, comprising:
   a circular carrier having a circle center and rotating around the circle center;
   an illuminator disposed at the circle center of the circular carrier and emitting incident light onto tissues under a surface of an object-to-be-detected; and
   a detector disposed on the circular carrier and performing a circular motion, with the illuminator as a center, around the illuminator in accordance with rotation of the circular carrier, wherein the detector receives diffuse light diffused from the incident light onto the tissues under the surface of the object-to-be-detected and generates sensing information of the tissues under the surface of the object-to-be-detected.

2. The rotation type optical scanner of claim 1, further comprising a drive mechanism that drives the circular carrier, wherein the drive mechanism is used to drive the circular carrier to rotate.

\* \* \* \* \*